(12) United States Patent
Strelchenok

(10) Patent No.: US 6,699,851 B2
(45) Date of Patent: Mar. 2, 2004

(54) CYTOTOXIC COMPOUNDS AND THEIR USE

(75) Inventor: Oleg Strelchenok, Lidingö (SE)

(73) Assignee: Ardenia Investments, Ltd., London (GB)

(*) Notice: Subject to any disclaimer, the term of this patent is extended or adjusted under 35 U.S.C. 154(b) by 0 days.

(21) Appl. No.: 10/332,745

(22) PCT Filed: Jul. 5, 2001

(86) PCT No.: PCT/SE01/01559

§ 371 (c)(1), (2), (4) Date: May 6, 2003

(87) PCT Pub. No.: WO02/04467

PCT Pub. Date: Jan. 17, 2002

(65) Prior Publication Data

US 2003/0171338 A1 Sep. 11, 2003

Related U.S. Application Data

(60) Provisional application No. 60/217,810, filed on Jul. 12, 2000.

(30) Foreign Application Priority Data

Jul. 12, 2000 (SE) .................................... 0002629

(51) Int. Cl.$^7$ ................................................ A01N 57/36

(52) U.S. Cl. ...................... 514/119; 514/613; 514/627; 514/109; 554/40; 564/15

(58) Field of Search .............................. 554/40; 514/109, 514/119, 627, 613; 564/15

(56) References Cited

FOREIGN PATENT DOCUMENTS

| WO | WO 99/65936 | 12/1999 |
|----|-------------|---------|
| WO | WO 00/42832 | 7/2000  |
| WO | WO 00/47589 | 8/2000  |

*Primary Examiner*—Deborah Carr
(74) *Attorney, Agent, or Firm*—Morrison & Foerster LLP

(57) ABSTRACT

Novel amides of polyunsaturated fatty acids with cysteamine-S-phosphate have been synthesized. Combinations of the all-trans-retinoic acid and/or amides of the 13-cis-retinoic acid with O-phospho-L-tyrosine, and N-docosahexaenoyl-cysteamine-S-phosphate, N-eicosapentaenoyl-cysteamine-S-phosphatee, N-arachidonoyl-cysteamine-S-phosphate, N-α-linolenoyl-cysteamine-S-phosphate, and N-γ-linolenoyl-cysteamine-S-phosphate and their analogues N-docosahexaenoyl-O-phospho-2-aminoethanol, N-eicosapentaenoyl-O-phospho-2-aminoethanol, N-arachidonoyl-O-phospho-2-aminoethanol, N-α-linolenoyl-O-phospho-2-aminoethanol, N-γ-linolenoyl-O-phospho-2-aminoethanol in different compositions exhibit a marked cell-growth inhibiting effect and display anti-tumor activity.

29 Claims, No Drawings

CYTOTOXIC COMPOUNDS AND THEIR USE

CROSS REFERENCE TO RELATED APPLICATIONS

This application is a U.S. National Phase application of International PCT/SE01/01559, filed Jul. 5, 2001, which claims priority to Swedish Patent Application Serial No. SE 0002629-4 filed on Jul. 12, 2000 and U.S. Provisional Application Ser. No. 60/217,810 filed on Jul. 12, 2000, all of which are hereby incorporated by reference in their entirety.

The present invention concerns novel amides and their use, in particular their therapeutic use. These compounds have been synthesised and characterised by the present inventor, as disclosed herein. Further, their efficacy as anti-tumour agents has been shown in vitro and in animal studies, disclosed in the attached examples.

BACKGROUND OF THE INVENTION

Tumour cell drug resistance is a major problem in cancer chemotherapy. With resistance development follows the necessity of increasing doses, combination therapies and other treatment regimens, often associated with severe side effects for the patient.

Studies concerning the cytotoxicity of essential fatty acids on cancer cell lines have been published by several working groups. Moreover, several experimental studies have shown that exogenous polyunsaturated fatty acids (PUFAs) may sensitise tumour cells to anti-cancer drugs in cell culture or in tumours growing in animals.

No precise mechanism of action of PUFAs in the modulation of anti-cancer drug efficacy has yet been determined. It has been proposed that the enhanced tumour cell killing effect of anti-cancer drugs could result from alterations in the biophysical properties and functions of membranes brought about by PUFA supplementation.

In addition to the effects of PUFAs on membrane structure, the peroxidation of highly unsaturated fatty acids has been linked to cytotoxicity in neoplastic cells In response to oxidative stress, PUFAs undergo free-radical chain reaction breakdown, which results in the formation of fatty acid hydroperoxides and hydroxides as immediate products and aldehydes, among other end-products. Both in cultured tumour cells and in tumour-bearing animals, PUFA supplementation has been shown to cause a decrease in cell proliferation or in tumour growth correlated with a concomitant increase in the level of cellular lipid peroxidation. These observations suggest that PUFAs interfere with tumour cell proliferation in vitro and in vivo due to the formation of oxidation products. Little is however known about the involvement of lipid peroxidation in the modulation of drug efficacy by PUFAs.

The ability of PUFAs to increase the cytotoxic activity of several anti-cancer drugs has been well documented. The involvement of lipid peroxidation as a potential mechanism through which PUFAs modulate the efficacy of those cytotoxic drugs has been suggested from experimental studies in tumour-bearing animals (Shao Y., et al., Lipids, 30, 1035–1045, 1995) or in cell culture (Petersen E. S., et al., Cancer Res., 42, 6263–6269, 1992) and showing that PUFAs in conjunction with oxidants strongly increase the activity of a cytotoxic drug that generates an oxidative stress and that lipid peroxidation may be involved in this effect (Germain E., et al., Int. J. Cancer, 75, 578–583, 1998).

These results coupled with the observation that various fatty acids can alter the activity of cell membrane bound enzymes such as sodium-potassium-ATPase and 5'-nucleotidase, levels of various anti-oxidants, p53 expression and the concentrations of protein kinase C suggest that essential fatty acids and their metabolites can reverse tumour cell drug-resistance at least in vitro. (Das U. N., et al., Prostaglandins Leukot. Essent. Fatty Acids, 58, 39–54, 1998).

The influence of different PUFAs on doxorubicin-induced cell toxicity has been examined (Germain E., et al., supra). In agreement with previous studies, it was observed that DHA was the most potent of all tested PUFAs at enhancing doxonibicin efficacy. For most of the PUFAs, the effect on drug activity increased with the double bond index. The only exception was 18:3n-6, which was more potent than 18:3n-3 and than fatty acids with 4 or 5 unsaturations (20:4n-6 or 20:5 n-3). This may be related to specific properties of 18:3n-6, as already documented in other cell lines.

In humans, little is known about the involvement of lipid peroxidation in drug efficacy. Exogenous PUFAs are readily incorporated into breast cancer cell membranes (Gore J., et al., Amer. J. Physiol., 266, C110–C120, 1994).

It remains to be determined to what extent the toxic side effects of known cytotoxic drugs (such as their hematological or cardiac toxicity) would be affected. This is required before any intervention trial involving such a strategy can be considered in human patients.

The problems underlying the present invention are manifold. One problem is how to modulate and preferably increase the efficacy of presently known cytotoxic agents with unchanged or preferably reduced side effects. The avoidance of systemic toxic effects and complications, such as hematological or cardiac toxicity is another problem of great importance.

Yet another problem is how to prevent the development of tumour cell drug resistance, which presently is a major complication in cancer chemotherapy. Further problems include how to locally focus the effect of cytotoxic drugs to the tumour cells or affected organs, and thus increase the efficacy of the treatment without negative consequences to the patient. Also knowing that some PUFAs have the ability to increase the cytotoxic activity of several anti-tumour drugs, it remains a problem to find and synthesize new, specific compounds, exhibiting either the ability to increase the cytotoxic activity of existing drugs or having a cytotoxic effect in themselves.

Further, it remains a problem how to design new combinations of specific compounds, both presently known and hitherto unknown compounds, exhibiting an enhanced anti-tumour effect.

SUMMARY OF THE INVENTION

The present inventor has surprisingly shown, that the disclosed amides of the docosahexaenoic acid and eicosapentaenoic acid and arachidonic acid, and α-linolenic acid or γ-linolenic acid with cysteamine-S-phosphate exert a significant cytotoxic action against tumour cells in vitro. During the priority year, these results have been confirmed in animal studies.

Combinations of the all-trans-retinoic acid and/or amides of the 13-cis-retinoic acid with 0-phospho-L-tyrosine, and N-docosahexaenoyl-cysteamine-S-phosphate, N-eicosapentaenoyl-cysteamine-S-phosphate, N-arachidonoyl-cysteamine-S-phosphate, N-α-linolenoyl-cysteamine-S-phosphate, and N-γ-linolenoyl-cysteamine-S-phosphate and their analogues N-docosahexaenoyl-O-phospho-2-aminoethanol, N-eicosapentaenoyl-O-phospho- 2-aminoethanol, N-arachidonoyl-O-phospho-2-aminoethanol, N-α-linolenoyl-O-phospho-2-aminoethanol, N-γ-linolenoyl-O-phospho-2-aminoethanol in different compositions exhibit a marked cell-growth inhibiting effect and display anti-tumour activity in in vivo and in vitro experiments.

The invention will be disclosed in closer detail in the following description and examples, to be read in connection with the attached claims, which are hereby incorporated in their entirety.

DESCRIPTION OF THE INVENTION

In the following description, the term "cancer" is used to define any uncontrolled cell growth, malignant or benign. The term "treatment" is used with the aim of comprising both active or curative treatment, as well as pallative treatment.

The term "cytotoxic agent" is used to define any pharmacologic compound that inhibits the proliferation of cells within the body, and in particular existing and future pharmaceuticals used in cancer theraphy. Doxorubicin (DXR) is a well known anthracyclin antibiotic, used in the treatment of a variety of malignant neoplastic diseases. In the present description, DXR is used as an example of a cytotoxic agent.

The novel compounds according to the present invention are amides of docosahexaenoic acid and eicosapentaenoic acid and arachidonic acid, and α-linolenic acid or γ-linolenic acid, with cysteamine-S-phosphate.

Specific novel compounds according to the present invention are for example (the compound number is given in parenthesis for easier reference):

N-docosahexaenoyl-cysteamine-S-phosphate (C1)
N-eicosapentaenoyl-cysteamine-S-phosphate (C2)
N-arachidonoyl-cysteamine-S-phosphate (C3)
N-α-linolenoyl-cysteamine-S-phosphate (C4)
N-γ-linolenoyl-cysteamine-S-phosphate (C5)

The following N-Acyl-O-phospho-2-aminoethanol analogues have been disclosed in PCT/IB99/02064 by the present inventor, but have now attracted renewed interest:

N-docosahexaenoyl-O-phospho-2-aminoethanol (C6)
N-eicosapentaenoyl O-phospho-2-aminoethanol (C7)
N-arachidonoyl O-phospho-2-aminoethanol (C8)
N-α-linolenoyl O-phospho-2-aminoethanol (C9)
N-γ-linolenoyl O-phospho-2-aminoethanol (C10)

The novel compounds (C1–C5) have been shown by the present inventor to exert a cytotoxic action against tumour cells in vitro.

It was also shown that a combination of any one of the novel compounds C1 through C5, or any one of their analogues N-Acyl-O-phospho-2-aminoethanol (C6 through C10) and N-(all-trans-retinoyl)-O-phospho-L-tyrosine (C11) or N-(13-cis-retinoyl)-O-phospho-L-tyrosine (C12) exert a pronounced cytotoxic action against tumour cells in vitro and also display anti-tumour activity in vivo.

A cytotoxicity assay of the preparations was carried out on the well-known HeLa cell line of human cervical carcinoma. The extent of cell growth inhibition caused by the assayed preparations was used to evaluation their cytotoxicity.

The extent of cell growth inhibition of these preparations at a final concentration of each compound in an interval from $5 \cdot 10^{-10}$ to $15 \cdot 10^{-10}$ mol/l is shown in table 1.

TABLE 1

Effect of HeLa cell growth inhibition

| First compound | Second compound | Inhibition (%) |
|---|---|---|
| C1 | — | 25.3% ($p < 0.02$) |
| C2 | — | 24.2% ($p < 0.01$) |
| C3 | — | 22.8% ($p < 0.05$) |
| C4 | — | 21.2% ($p < 0.05$) |
| C5 | — | 20.1% ($p < 0.05$) |
| C1 | C11 | 64.6% ($p < 0.001$) |
| C1 | C12 | 61.3% ($p < 0.001$) |
| C2 | C11 | 62.5% ($p < 0.001$) |
| C2 | C12 | 60.2% ($p < 0.001$) |
| C3 | C11 | 59.6% ($p < 0.001$) |
| C3 | C12 | 55.4% ($p < 0.001$) |
| C4 | C11 | 56.9% ($p < 0.001$) |
| C4 | C12 | 55.2% ($p < 0.001$) |
| C5 | C11 | 57.4% ($p < 0.001$) |
| C5 | C12 | 53.7% ($p < 0.001$) |
| C6 | C11 | 45.3% ($p < 0.01$) |
| C6 | C12 | 42.7% ($p < 0.01$) |
| C7 | C11 | 43.5% ($p < 0.01$) |
| C7 | C12 | 40.1% ($p < 0.01$) |
| C8 | C11 | 37.4% ($p < 0.01$) |
| C8 | C12 | 35.7% ($p < 0.02$) |
| C9 | C11 | 35.8% ($p < 0.01$) |
| C9 | C12 | 30.2% ($p < 0.02$) |
| C10 | C11 | 33.1% ($p < 0.01$) |
| C10 | C12 | 31.5% ($p < 0.02$) |

Compounds C1 through C10 are analogues of lysophosphatidate (LPA). Lysophosphatidate is known to be an intercellular phospholipid messenger with a wide range of biological effects (Nietgen G. W., Durieux M. E., Cell Adhesion and Communication, 5, 221–235, 1998). In particular, a number of tumour-derived cells were growth-inhibited by LPA. LPA has antimitogenic properties in myeloma cell lines and induces a pertussis toxin-insensitive increase in cAMP. Together with the findings in Jurkat T-cell lymphoma and primary astrocyte cell lines, where LPA is ineffective in altering cell proliferation this suggests that LPA might play a role as a regulator of cell proliferation. Probably, both the inhibitory action of LPA on tumour cells and the inhibition of HeLa cells proliferation by compounds C1–C5 proceed by a similar mechanism.

The compounds C11 and C12 can be regard as low-molecular-mass interceptors, blocking signaling protein kinases or activating signalling protein phosphatases in tumour cells. Combinations of the compounds C1 through C10 and C11 (C12) in different compositions have here been shown to have a surprising and significantly increased cytostatic effect as compared to compounds C1–C10 alone and C11 (C12) alone. One explanation to this phenomenon, according to the present inventor, could be the following: the action of compounds C1–C10 and C11 (C12) follow different signalling pathways simultaneously and this results in an enhancement of cancer cell growth inhibition.

The compounds according to the invention can be used as such or as components in pharmaceutical compositions, for example in admixture or association with presently known cytotoxic agents.

Doxorubicin is an aminoglycosidic anthracycline antibiotic and will be used as a typical representative of this group of compounds.

The compositions C1+C11, C2+C11, C3+C11 C4+C11, C5+C11 and C1+C12 C2+C12, C3+C12, C4+C12, C5+C12 display marked anti-tumour action against Ehrlich ascites carcinoma (EAC) in mice. The extent of tumour inhibition is close to 30%.

The compositions C6+C11, C7+C11, C8+C11, C9+C11, C10+C11 and C6+C12, C7+C12, C8+C12, C9+C12, C10+

C12 display pronounced anti-tumour action against EAC in mice. The extent of tumour inhibition is over the range from 20% to 30%. The pretreatment with the compositions C6+C11, C7+C11, C8+C11, C9+C11, C10+C11 and C6+C12, C7+C12, C8+C12, C9+C12, C10+C12 display marked increase of anti-tumour action of DXR against EAC in mice. The extent of tumour inhibition compared to that of DXR is increased ranging from 25% to 40%.

The novel compounds (C1–C5) exhibit good solubility in water due to the presence of the phosphate groups in the molecules. The critical micelle concentration (CMC) values for compounds 1 through 5 were determined as described by A. Chattopadhyay and E. London (Anal.Biochem., 1984, 139, p.408–412). The CMC values for ammonia salts of compounds 1 through 5 (C1–C5) are over the range $1,1 \times 10^{-4} – 1,8 \times 10^{-4}$ M. In the present experiments, the compounds 1 through 10 (C1–C10) were dissolved in normal mice serum and exhibited cell-growth inhibiting effects and displayed anti-tumour activity in micelle form.

The compounds according to the invention can be used as such or as components in pharmaceutical compositions. The compounds can be given systemically or locally, for example topically. Suitable modes of administration of the compounds include intravenous administration, intraperitoneal administration, as well as oral, rectal and transdermal administration. The compounds according to the invention can be administered alone or in combination with other pharmaceuticals, before, during or after surgical treatment or independently thereof.

The intended mode of administration is naturally taken into account in the preparation of the final pharmaceutical composition. Normal pharmaceutical adjuvants can naturally be used and the compounds can be made available in the form of injectable solutions, ointments, capsules or tablets, in the form of transdermal patches or suppositories according to the intended use and/or mode of administration.

The therapeutic effective doses for intravenous administration of the compounds are in intervals:

Compounds C1 through C5: from about 2 mg/kg to about 5 mg/kg body weight

Compounds C6 through C10: from about 5 mg/kg to about 10 mg/kg body weight

Compounds C11 and C12: from about 5 mg/kg to about 30 mg/kg body weight

The compounds can be given systemically or locally, for example topically on the skin or injected in a tumour or in an organ, affected by cancer. Suitable modes of administration of the compounds include intravenous administration, intramuscular administration, local injection, intraperitoneal administration, as well as oral, rectal and transdermal administration. The intended mode of administration is naturally taken into account in the preparation of the final pharmaceutical composition. Normal pharmaceutical adjuvants can naturally be used and the compounds can be made available in the form of injectable solutions, slow release preparations, ointments, capsules or tablets, in the form of transdermal patches or suppositories according to the intended use and/or mode of administration.

It is possible to administer the inventive compound or mixture of compounds before, substantially simultaneously or after administration of a cytotoxic agent, for example doxorubicin. Preferably, the compounds of the present invention are administered before or substantially simultaneously with the cytotoxic agent, most preferably in admixture therewith.

EXAMPLES

A: Synthesis

Example 1

Synthesis of the N-(cis-5,8,11,14-eicosatetraenoyl)-cysteamine-S-phosphate (N-arachidonoyl-cysteamine-S-phosphate) (C3)

a) "Phosphorylating Agent":

Phosphorus trichloride (1.38 mg, 10 mmol) and triethylamine (2.53 mg, 25 mmol) were dissolved in 10 ml of dry tetrahydrofuran and chilled to −15° C., then t-butanol (2.97 mg, 40 mmol) and triethylamine (2.53 mg, 25 mmol) in 10 ml of dry tetrahydrofuran were added. After 10 min, the mixture free of precipitated triethylamine hydrochloride was filtered through aluminium oxide (basic, Brockmann II), evaporated to dryness and dissolved in 2 ml dry benzene.

b) Arachidonic acid (152 mg, 0.5 mmol) and triethylamine (52 mg, 0.51 mmol) were dissolved in 3 ml of dry acetonitrile and chilled to −15° C., and 70 mg (0.51 mmol) of butyl chloroformate was added. After 30 min, the mixture free of the precipitated triethylamine hydrochloride was pipetted in a solution of cystamine dihydrochloride (56 mg, 0.25 mmol) and triethylamine (52 mg, 0.51 mmol) in 1 ml of methanol, stirring was continued for 15 min at −15° C., then the mixture obtained was allowed to warm to room temperature. After 2 h, 0.5 M HCl was added, and the mixture was extracted with ether (20 ml). The extract was washed with water, then dried with $Na_2SO_4$, and evaporated under reduced pressure. The residue was dissolved in 2 ml of chloroform and purified by column (2×2 cm) chromatography on aluminium oxide (basic, Brockmann II). Elution of the column with chloroform-methanol (9:1 v/v) and evaporation of the appropriate fractions gave 181 mg (75%) of the desired N,N'-diarachidonoylcystamine as a waxy solid: TLC, Merck silica gel 60 pre-coated plates [system A: benzen-dioxan-acetic acid (25:5:1 v/v/v)] $R_f$ 0.5.

The solution of N,N'-diarachidonoylcystamine in 2 ml of dry benzene was added to the solution of "phosphorylating agent". The reaction mixture was stirred for 4 days at 20° C., evaporated to dryness, dissolved in 1 ml of benzene, and trifluoroacetic acid (114 mg, 1 mmol) was added. After 20 h at room temperature the reaction mixture was concentrated in vacuo and applied to a column of silica gel. The desired product was eluted from column with chloroform-methanol (30-20: 70-80, v/v), the fractions containing pure substance stained on the TLC plates with molybdate spray were combined and evaporated to dryness to give 53 mg (24%) of (C3): $R_f$ 0.15–0.20 [system B: chloroform-methanol-$NH_3$ aq (9:7:2 v/v/v)] $^1$H-NMR ($CD_3SOCD_3$, 200 MHz) δ0.9–1.0 (t, 3H, ω-$CH_3$); 1.3 (s, 8H, 4$CH_2$); 2.0–2.2 (m, 6H, 2$CH_2CH=CH$ and $CH_2CO$); 2.6–2.9 (m, 8H, $CH_2SP$ and 3HC=CHC$H_2$CH=CH); 3.2–3.3 (br s, 2H, $CH_2NH$); 5.2–5.4 (br s, 8H, 4HC=CH); 8.3–8.5 (m, 3H, NH and 2POH).

Example 2

Synthesis of the N-(cis-4,7,10,13,16,19-docosahexaenoyl)-cysteamine-S-phosphate (C1)

This compound was prepared as described above for compound 3 (C3) above, using 0.5 mmol (164 mg) of cis-4,7,10,13,16,19-docosahexaenoic acid; yield, 58 mg (25%); $R_f$ 0.15–0.20 (system B); $^1$H-NMR ($CD_3SOCD_3$, 200 MHz) δ0.9–1.0 (t, 3H, ω-$CH_3$);2.0–2.1 (t, 2H, $CH_2CO$); 2.2–2.4 (m, 4H, 2$CH_2CH=CH$); 2.6–2.9 (m, 12H, $CH_2SP$ and 5HC=CHC$H_2$CH=CH); 3.2–3.3 (br s, 2H, $CH_2NH$); 5.2–5.4 (br s, 12H, 6HC=CH); 8.3–8.5 (m, 3H, NH and 2POH).

Example 3
Synthesis of the N-(cis-5,8,11,14,17-eicosapentaenoyl)-cysteamine-S-phosphate (C2)

This compound was prepared as described above for compound 3 (C3) using 0.5 mmol (151 mg) of cis-5,8,11,14,17-eicosapentaenoic acid; yield 57 mg (26%); $R_f$ 0.15–0.20 (system B); $^1$H-NMR (CD$_3$SOCD$_3$, 200 MHz) δ0.9–1.0 (t, 3H, ω-CH$_3$); 1.5–1.6 (t, 2H, CH$_2$); 2.0–2.2(m, 6H, CH$_2$CO and 2CH$_2$CH=CH); 2.6–2.9 (m, 10H, CH$_2$SP and 4HC=CH—CH$_2$—CH=CH); 3.2–3.3 (br s, 2H, CH$_2$NH); 5.2–5.4 (br s, 10H, 5HC=CH); 8.3–8.5 (m, 3H, NH and 2POH).

Example 4
Synthesis of the N-(cis-9,12,15-octadecatrienoyl)-cysteamine-S-phosphate (N-α-linolenoyl-cysteamine-S-phosphate) (C4)

This compound was prepared as described above for (C3), using 0.5 mmol (139 mg) of cis-9,12,15-octadecatrienoic acid; yield 42 mg (20%); $R_f$ 0.15–0.20 (system B); $^1$H-NMR (CD$_3$SOCD$_3$, 200 MHz) δ0.9–1.0 (t, 3H, ω-CH$_3$); 1.3 (s, 8H, 4CH$_2$); 1.4–1.5 (br s, 2H, CH$_2$CH$_2$CO); 2.0–2.2 (m, 6H, CH$_2$CO and 2CH$_2$CH=CH); 2.6–2.9 (m, 6H, CH$_2$SP and 2HC=CH—CH$_2$—CH=CH); 3.1–3.2 (br s, 2H, CH$_2$NH); 5.2–5.4 (br s, 6H, 3HC=CH); 8.3–8.5 (m, 3H, NH and 2POH).

Example 5
Synthesis of the N-(cis-6,9,12-octadecatrienoyl)-cysteamine-S-phosphate (N-γ-linolenoyl-cysteamine-S-phosphate) (C5)

This compound was prepared as described above for (C3), using 0.5 mmol (139 mg) of cis-6,9,12-octadecatrienoic acid; yield 46 mg (22%); $R_f$ 0.15–0.20 (system B); $^1$H-NMR (CD$_3$SOCD$_3$, 200 MHz) δ0.9–1.0 (t, 3H, ω-CH$_3$); 1.3 (s, 8H, 4CH$_2$); 1.4–1.5 (br s, 2H CH$_2$CH$_2$CO); 2.0–2.2 (m, 6H, CH$_2$CO and 2CH$_2$CH=CH); 2.6–2.9 (m, 6H, CH$_2$SP and 2HC=CH—CH$_2$—CH=CH); 3.1–3.2 (br s, 2H, CH$_2$NH); 5.2–5.4 (br s, 6H, 3HC=CH); 8.3–8.5 (m, 3H, NH and 2POH).

Example 6
Synthesis of the N-Acyl-cysteamine-S-phosphate
Were Acyl is:
cis-4,7,10,13,16,19-docosahexaenoyl (C1)
cis-5,8,11,14,17-eicosapentaenoyl (C2)
cis-5,8,11,14-eicosatetraenoyl (arachidonoyl) (C3)
cis-9,12,15-octadecatrienoyl (α-linolenoyl) (C4)
cis-6,9,12-octadecatrienoyl (γ-linolenoyl) (C5)

Polyunsaturated acid (1 mmol) and triethylamine (103 mg, 1.02 mmol) were dissolved in 2 ml of dry tetrahydrofuran, then dry acetonitrile (4 ml) was added, the mixture chilled to −15° C., and 139 mg (1.02 mmol) of butyl chloroformate was added. After 30 min, the mixture free of the precipitated triethylamine hydrochloride was pipetted in a solution of cysteamine-S-phosphate ("Sigma-Aldrich", 269 mg, 1.5 mmol) in 3 ml of 1M Na$_2$CO$_3$ and 3 ml of H$_2$O. The mixture obtained was stirred for 1 h at 20–25° C., acidified with 1M HCl to pH 2–3 and extracted with chloroform-methanol (2:1, v/v). The extract was washed with methanol-water (10:9, v/v), concentrated under reduced pressure and dissolved in chloroform-methanol-NH$_3$ aq (13:5:1, v/v/v). The solution obtained was evaporated under reduced pressure and dissolved in ethanol-water (2:3, v/v, 15ml). The emulsion obtained was washed with ether (2×10 ml) and evaporated under reduced pressure gave the ammonium salt of N-acyl-cysteamine-S-phosphate.

Yields: 74% (C1); 76% (C2); 72% (C3); 71% (C4); 70% (C5).

All the products obtained are identical to the compounds prepared by the method using the "phosphorylating agent" for phosphorylation of the N-acyl derivatives.

For the $^1$H-NMR-spectral analysis, ammonium salts were converted into acidified forms by means of washing of the chloroform-methanol (2:1, v/v) solutions with 1M HCl.

Example 7
Synthesis of the N-Acyl-O-Phospho-2-Aminoethanol
Were Acyl is:
cis-4,7,10,13,16,19-docosahexaenoyl (C6)
cis-5,8,11,14,17-eicosapentaenoyl (C7)
cis-5,8,11,14-eicosatetraenoyl (arachidonoyl) (C8)
cis-9,12,15-octadecatrienoyl (α-linolenoyl) (C9)

Polyunsaturated acid (1 mmol) and triethylamine (103 mg, 1.02 mmol) were dissolved in 2 ml of dry tetrahydrofuran, then dry acetonitrile (4 ml) was added, the mixture chilled to −15° C., and 139 mg (1.02 mmol) of butyl chloroformate was added. After 30 min, the mixture free of the precipitated triethylamine hydrochloride was pipetted in a solution of O-phosphorylethanolamine ("Sigma-Aldrich") (212 mg, 1.5 mmol) in 3 ml of 1M Na$_2$CO$_3$ and 3 ml of H$_2$O. The mixture obtained was stirred for 1 h at 20–25° C., acidified with 1M HCl to pH 2–3 and extracted with chloroform-methanol (2:1, v/v). The extract was washed with methanol-water (10:9, v/v), concentrated under reduced pressure and dissolved in chloroform-methanol-NH$_3$ aq (13:5:1, v/v/v). The solution obtained was evaporated under reduced pressure and dissolved in ethanol-water (2:3, v/v, 15 ml). The emulsion obtained was washed with ether (2×10 ml) and evaporated under reduced pressure gave the ammonium salt of N-acyl-O-phospho-2-aminoethanol.

Yields: 88% (C6); 83% (C7); 84% (C8); 73% (C9).

All the products obtained are identical to the compounds prepared by the method using β-cyanoethyl phosphate for phosphorylation of the N-acyl derivatives.

For the $^1$H-NMR-spectral analysis, ammonium salts were converted into acidified forms by means of washing of the chloroform-methanol (2:1, v/v) solutions with 1M HCl.

$^1$H-NMR-spectra data for the compounds C6–C9 have been disclosed in the international application PCT/IB99/02064 by the same inventor.

Example 8
Synthesis of the N-(cis-6,9,12-octadecatrienoyl)-O-phospho-2-aminoethanol (N-γ-linolenoyl-O-phospho-2-aminoethanol) (C10)

This compound was prepared as described above (example 7), using 0.5 mmol (139 mg) of cis-6,9,12-octadecatrienoic acid; yield 84 mg (42%); $R_f$ 0.10–0.15 [system B: chloroform-methanol-NH$_3$ aq (9:7:2 v/v/v)]; $^1$H-NMR (CD$_3$SOCD$_3$, 200 MHz) δ0.9–1.0 (t, 3H, ω-CH$_3$); 1.3 (s, 8H, 4CH$_2$); 1.4–1.5 (br s, 2H, CH$_2$CH$_2$CO); 2.0–2.2 (m, 6H, CH$_2$CO and 2CH$_2$CH=CH); 2.7–2.9 (br s, 4H, 2HC=CH—CH$_2$—CH=CH); 3.1–3.2 (br s, 2H, CH$_2$NH); 3.7–3.8 (br s, 2H, CH$_2$OP); 5.2–5.4 (br s, 6H, 3HC=CH); 8.2–8.4 (m, 3H NH and 2POH).

Example 9
Synthesis of the N-Retinoyl-O-Phospho-L-Tyrosine
Were Retinoyl is:
all-trans-Retinoyl (C11)
13-cis-Retinoyl (C12)

Retinoic acid (1 mmol) and triethylamine (103 mg, 1.02 mmol) were dissolved in 6 ml of tetrahydrofuran, the mixture chilled to −15° C., and 139 mg (1.02 mmol) of butyl chloroformate was added. After 30 min, the mixture was added to the solution of 261 mg (1 mmol) of O-phospho-L-tyrosine ("Sigma-Aldrich") in 3 ml of 1M $Na_2CO_3$ and 3 ml of $H_2O$ Then 3 ml of EtOH was added. The mixture obtained was stirred for 4 h at 20–25° C., acidified with 1M HCl to pH 2–3 and extracted with chloroform-methanol (2:1, v/v). The extract was washed with methanol-water (10:9, v/v), concentrated under reduced pressure and dissolved in chloroform-methanol-$NH_3$ aq (13:5:1, v/v/v). The solution obtained was evaporated under reduced pressure and dissolved in ethanol-water (2:3, v/v, 15 ml). The emulsion obtained was washed with ether (5×10 ml) and evaporated under reduced pressure gave the ammonium salt of N-retinoyl-O-phospho-L-tyrosine.

Yields: 52% (C11); 49% (C12).

All the products obtained are identical to the compounds prepared by the method using βcyanoethyl phosphate for phosphorylation of the N-acyl derivatives.

For the $^1$H-NMR-spectral analysis, ammonium salts were converted into acidified forms by means of washing of the chloroform-methanol (2:1, v/v) solutions with 1M HCl. $^1$H-NMR-spectra data for compounds C11 and C12 have been disclosed in the international application PCT/IB99/02064 by the same inventor.

B: Assay of Cytotoxicity

Materials and Methods

The assay of cytotoxicity of the inventive preparations was carried out on the well-known human cervical carcinoma cell line HeLa. HeLa cells were cultivated in full cultivation medium, containing 80% of Eagle Minimal Essential Medium with glutamine (Sigma), 20% of normal bovine serum, penicillin 100 IE/ml and streptomycin 100 μg/ml. HeLa cell at concentration of $10^5$ cells/ml were seed in 24-well plates for adhesive cell lines (Sarstedt) in volume of 2 ml per well. HeLa cells were cultivated in $CO_2$-incubator at temperature 37° C. in humidified atmosphere, consisting of 95% air and 5% $CO_2$. On the next day, the experimental cultures were supplemented with solutions of the inventive preparations in normal bovine serum (NBS) in a volume of 20 μl, in order to obtain the necessary concentration for studying these in cultures. Control cultures were supplemented with normal bovine serum. After that HeLa cells were cultivated two days again at the same conditions. On the third day, HeLa cells from each cultures were harvested separately using versen. The number of viable cells was counted using tryphan blue exclusion test and a hemocytometer.

For evaluation of the cytotoxic action of these assayed preparations on HeLa cells the means value and standard errors of means of viable cell numbers were calculated. The cell growth inhibition (%) was calculated as:

$$\frac{Control - Experimental}{Control} \cdot 100$$

The extent of cell growth inhibition caused by the assayed preparations was used for evaluation of their cytotoxicity.

Results cl Example 10

Evaluation of the Cytotoxicity of Compounds C1, C2, C3, C4 and C5 in Cell Cultures of HeLa Human Cervical Carcinoma After cultivation of the HeLa cells for 24 h, the assayed cultures were treated with solutions of C1, C2, C3, C4 and C5 in normal bovine serum (NBS). The initial solutions of the compounds C1, C2, C3, C4 and C5 in NBS had a concentration equal to 0.5 mg/ml. From those solutions two working solutions of each preparation for adding to cultures were prepared:

C1: $5.93 \times 10^{-8}$ and $11.85 \times 10^{-8}$ mol/l;
C2: $6.25 \times 10^{-8}$ and $12.50 \times 10^{-8}$ mol/l;
C3: $6.23 \times 10^{-8}$ and $12.45 \times 10^{-8}$ mol/l;
C4: $6.59 \times 10^{-8}$ and $13.17 \times 10^{-8}$ mol/l;
C5: $6.59 \times 10^{-8}$ and $13.17 \times 10^{-8}$ mol/l.

Aliquots (20 μl) of these working solutions were added to 2 ml cultures of HeLa cells to a final concentration in the cultures:

C1: $5.93 \times 10^{-10}$ and $11.85 \times 10^{-10}$ mol/l;
C2: $6.25 \times 10^{-10}$ and $12.50 \times 10^{-10}$ mol/l;
C3: $6.23 \times 10^{-10}$ and $12.45 \times 10^{-10}$ mol/l;
C4: $6.59 \times 10^{-10}$ and $13.17 \times 10^{-10}$ mol/l;
C5: $6.59 \times 10^{-10}$ and $13.17 \times 10^{-10}$ mol/l.

In the control cultures, 20 μl of NBS was added as a solvent control. After two days of following cultivation the number of living cells in the cultures was counted and the extent of growth inhibition of HeLa cells was calculated in order to evaluate the cytotoxicity of the assayed preparations.

After tree days of cultivation, the control cultures contained $(454.4 \pm 21.75) \times 10^3$ cells.

The treated cultures in the first and second series of concentrations had the following number of living cells:

C1: $(339.4 \pm 26.91) \times 10^3$, cell growth inhibition was 25.3% ($p<0.02$) and $(344.9 \pm 28.45) \times 10^3$, cell growth inhibition was 24.1% ($p<0.02$);

C2: $(347.2 \pm 26.54) \times 10^3$, cell growth inhibition was 23.6% ($p<0.02$) and $(344.3 \pm 22.31) \times 10^3$, cell growth inhibition was 24.2% ($p<0.01$);

C3: $(357.2 \pm 32.66) \times 10^3$, cell growth inhibition was 21.4% ($p<0.05$) and $(350.8 \pm 30.62) \times 10^3$, cell growth inhibition was 22.8% ($p<0.05$);

C4: $(360.8 \pm 30.47) \times 10^3$, cell growth inhibition was 20.6% ($p<0.05$) and $(358.1 \pm 27.23) \times 10^3$, cell growth inhibition was 21.2% ($p<0.05$);

C5: $(364.4 \pm 29.72) \times 10^3$, cell growth inhibition was 19.8% ($p<0.05$) and $(363.1 \pm 26.34) \times 10^3$, cell growth inhibition was 20.1% ($p<0.05$);

Thus, the preparations of C1, C2, C3, C4 and C5 that were added alone to cultures in small concentrations, exert a marked cytotoxic action against human tumour cells since the number of cells in the treated cultures is significantly reduced, compared to that of the controls.

Example 11

The Cytotoxicity of Preparations C6, C8 and C11 in Cultures of HeLa Cell Line of Human Cervical Carcinoma After cultivation of HeLa cells for 24 h, the assayed cultures were treated with solutions of C6, C8 and C11 in NBS. Initial solutions of preparations C6, C8 and C11 in NBS had a concentration equal to 0.5 mg/ml. From those solutions two working solutions of each preparation were prepared for adding to the cultures:

C6: $6.12 \times 10^{-8}$ and $12.25 \times 10^{-8}$ mol/l;
C8: $6.44 \times 10^{-8}$ and $12.88 \times 10^{-8}$ mol/l;
C11: $5.00 \times 10^{-8}$ and $10.00 \times 10^{-8}$ mol/l.

20 μl aliquots of these working solutions were added to 2 ml cultures of HeLa cells to a final concentrations in the first and second series of cultures:

C6: $6.12 \times 10^{-10}$ and $12.25 \times 10^{-10}$ mol/l;
C8: $6.44 \times 10^{-10}$ and $12.88 \times 10^{-10}$ mol/l;
C11: $5.00 \times 10^{-10}$ and $10.00 \times 10^{-10}$ mol/l.

In the control cultures, 20 µl of NBS was added as a solvent control. After two days of following cultivation, the number of living cells in cultures was counted and the extent of growth inhibition of HeLa cells was calculated for evaluating the cytotoxicity of the assayed preparations.

After tree days of cultivation, the control cultures contained $(454.4 \pm 21.75) \times 10^3$ cells.

Treated cultures in the first and second series of concentrations had the following number of living cells:

C6: $(424.2 \pm 18.41) \times 10^3$, cell growth inhibition was 6.6% (p>0.05) and $(420.8 \pm 27.79) \times 10^3$, cell growth inhibition was 7.4% (p>0.05);

C8: $(440.8 \pm 25.52) \times 10^3$, cell growth inhibition was 3.0% (p>0.05) and $(427.5 \pm 26.54) \times 10^3$, cell growth inhibition was 5.9% (p>0.05);

C11: $(376.7 \pm 24.52) \times 10^3$, cell growth inhibition was 17.1% (p>0.05) and $(430.8 \pm 16.37) \times 10^3$, cell growth inhibition was 5.2% (p>0.05);

Thus, preparations of C6, C8 and C11 that were added alone to cultures in small concentrations, did not exert the marked cytotoxic action against human tumor cells since the number of cells in treated cultures did not differ significantly from the controls.

Example 12
The Cytotoxicity of Preparations of C1+C11, C2+C11, C3+C11, C4+C11 and C5+C11 in Cultures of HeLa Cell Line of Human Cervical Carcinoma After cultivation of HeLa cells for 24 h, the assayed cultures were treated with solutions of preparations C1+C11, C2+C11, C3+C11, C4+C11 and C5+C11 in NBS. Initial solutions of preparations had a concentration of C1, C2, C3, C4, C5 and C11 equal to 0.5 mg/ml. From those solutions, working solutions of each preparation in NBS was prepared for adding to cultures:

C1+C11: $5.93 \times 10^{-8}$ mol/l of C1 and $5.00 \times 10^{-8}$ mol/l of C11;
C2+C11: $6.25 \times 10^{-8}$ mol/l of C2 and $5.00 \times 10^{-8}$ mol/l of C11;
C3+C11: $6.23 \times 10^{-8}$ mol/l of C3 and $5.00 \times 10^{-8}$ mol/l of C11;
C4+C11: $6.59 \times 10^{-8}$ mol/l of C4 and $5.00 \times 10^{-8}$ mol/l of C11;
C5+C11: $6.59 \times 10^{-8}$ mol/l of C5 and $5.00 \times 10^{-8}$ mol/l of C11.

20 µl aliquots of these working solutions were added to 2 ml cultures of HeLa cells to a final concentration in the cultures:

C1+C11: $5.93 \times 10^{-10}$ mol/l of C1 and $5.00 \times 10^{-10}$ mol/l of C11;
C2+C11: $6.25 \times 10^{-10}$ mol/l of C2 and $5.00 \times 10^{-10}$ mol/l of C11;
C3+C11: $6.23 \times 10^{-10}$ mol/l of C3 and $5.00 \times 10^{-10}$ mol/l of C11;
C4+C11: $6.59 \times 10^{-10}$ mol/l of C4 and $5.00 \times 10^{-10}$ mol/l of C11;
C5+C11: $6.59 \times 10^{-10}$ mol/l of C5 and $5.00 \times 10^{-10}$ mol/l of C11.

In the control cultures, 20 µl of NBS was added as a solvent control. After two days of following cultivation, the number of living cells in the cultures was counted and the extent of growth inhibition of HeLa cells was calculated for evaluating the cytotoxicity of the assayed preparations.

After tree days of cultivation, the control cultures contained $(421.9 \pm 29.38) \times 10^3$ cells.

The treated cultures had the following number of living cells:

C1+C11: $(149.4 \pm 24.96) \times 10^3$, cell growth inhibition was 64.6% (p<0.001);
C2+C11: $(158.1 \pm 25.27) \times 10^3$, cell growth inhibition was 62.5% (p<0.001);
C3+C11: $(170.6 \pm 23.34) \times 10^3$, cell growth inhibition was 59.6% (p<0.001);
C4+C11: $(181.9 \pm 29.39) \times 10^3$, cell growth inhibition was 56.9% (p<0.001);
C5+C11: $(179.7 \pm 27.30) \times 10^3$, cell growth inhibition was 57.4% (p<0.001).

Thus, preparations of C1+C11, C2+C11, C3+C11, C4+C11 and C5+C11 that were added to cultures in small concentrations, exert the pronounced cytotoxic action against human tumor cells since the number of cells in treated cultures was significantly decreased as compared to controls.

Example 13
The Cytotoxicity of Preparation of C1+C12, C2+C12, C3+C12, C4+C12 and C5+C12 in Cultures of HeLa Cell Line of Human Cervical Carcinoma After cultivation of HeLa cells for 24 h, the assayed cultures were treated with solutions of preparations C1+C12, C2+C12, C3+C12, C4+C12 and C5+C12 in NBS. The initial solutions of the preparations had a concentration of C1, C2, C3, C4, C5 and C12 equal to 0.5 mg/ml. From those solutions working solutions of each preparation in NBS was prepared for adding to the cultures:

C1+C12: $5.93 \times 10^{-8}$ mol/l of C1 and $5.00 \times 10^{-8}$ mol/l of C12;
C2+C12: $6.25 \times 10^{-8}$ mol/l of C2 and $5.00 \times 10^{-8}$ mol/l of C12;
C3+C12: $6.23 \times 10^{-8}$ mol/l of C3 and $5.00 \times 10^{-8}$ mol/l of C12;
C4+C12: $6.59 \times 10^{-8}$ mol/l of C4 and $5.00 \times 10^{-8}$ mol/l of C12;
C5+C12: $6.59 \times 10^{-8}$ mol/l of C5 and $5.00 \times 10^{-8}$ mol/l of C12.

20 µl aliquots of these working solutions were added to 2 ml cultures of HeLa cells to a final concentration in the cultures:

C1+C12: $5.93 \times 10^{-10}$ mol/l of C1 and $5.0 \times 10^{-10}$ mol/l of C12;
C2+C12: $6.25 \times 10^{-10}$ mol/l of C2 and $5.00 \times 10^{-10}$ mol/l of C12;
C3+C12: $6.23 \times 10^{-10}$ mol/l of C3 and $5.00 \times 10^{-10}$ mol/l of C12;
C4+C12: $6.59 \times 10^{-10}$ mol/l of C4 and $5.00 \times 10^{-10}$ mol/l of C12;
C5+C12: $6.59 \times 10^{-10}$ mol/l of C5 and $5.00 \times 10^{-10}$ mol/l of C12.

In the control cultures, 20 µl of NBS was added as a solvent control. After two days of following cultivation the number of living cells in cultures was counted and the extent of growth inhibition of HeLa cells was calculated for evaluating the cytotoxicity of the assayed preparations.

After tree days of cultivation, the control cultures contained $(447.5 \pm 33.02) \times 10^3$ cells.

The treated cultures had the following number of living cells:

C1+C12: $(173.1 \pm 24.13) \times 10^3$, cell growth inhibition was 61.3% (p<0.001);

C2+C12: (178.1±26.24)×10³, cell growth inhibition was 60.2% (p<0.001);

C3+C12: (199.4±23.14)×10³, cell growth inhibition was 55.4% (p<0.001);

C4+C12: (200.6±21.61)×10³, cell growth inhibition was 55.2% (p<0.001);

C5+C12: (207.2±18.75)×10³, cell growth inhibition was 53.7% (p<0.001).

Thus, the preparations of C1+C12, C2+C12, C3+C12, C4+C12 and C5+C12 that were added to cultures in small concentrations, exert a pronounced cytotoxic action against human tumour cells since the number of cells in the treated cultures was significantly decreased as compared to controls.

Example 14

The Cytotoxicity of Preparations C6+C11, C7+C11, C8+C11, C9+C11 and C10+C11 in Cultures of HeLa Cell Line of Human Cervical Carcinoma After cultivation of HeLa cells for 24 h, the assayed cultures were treated with solutions of preparations C6+C11, C7+C11, C8+C11, C9+C11 and C10+C11 in NBS. The initial solutions of the preparations had a concentration of C6, C7, C8, C9, C10 and C11 equal to 0.5 mg/ml. From those solutions working solutions of each preparation in NBS were prepared for adding to cultures:

C6+C11: $6.12 \times 10^{-8}$ mol/l of C6 and $5.00 \times 10^{-8}$ mol/l of C11;

C7+C11: $6.47 \times 10^{-8}$ mol/l of C7 and $5.00 \times 10^{-8}$ mol/l of C11;

C8+C11: $6.44 \times 10^{-8}$ mol/l of C8 and $5.00 \times 10^{-8}$ mol/l of C11;

C9+C11: $6.83 \times 10^{-8}$ mol/l of C9 and $5.00 \times 10^{-8}$ mol/l of C11;

C10+C11: $6.83 \times 10^{-8}$ mol/l of C10 and $5.00 \times 10^{-8}$ mol/l of C11.

20 μl aliquots of these working solutions were added to 2 ml cultures of HeLa cells to a final concentration in cultures:

C6+C11: $6.12 \times 10^{-10}$ mol/l of C6 and $5.00 \times 10^{-10}$ mol/l of C11;

C7+C11: $6.47 \times 10^{-10}$ mol/l of C7 and $5.00 \times 10^{-10}$ mol/l of C11;

C8+C11: $6.44 \times 10^{-10}$ mol/l of C8 and $5.00 \times 10^{-10}$ mol/l of C11;

C9+C11: $6.83 \times 10^{-10}$ mol/l of C9 and $5.00 \times 10^{-10}$ mol/l of C11;

C10+C11: $6.83 \times 10^{-10}$ mol/l of C10 and $5.00 \times 10^{-10}$ mol/l of C11.

In the control cultures, 20 μl of NBS was added as a solvent control. After two days of following cultivation the number of living cells in cultures was counted and the extent of growth inhibition of HeLa cells was calculated for evaluating the cytotoxicity of the assayed preparations.

After tree days of cultivation, the control cultures contained (380.6±18.15)×10³ cells.

The treated cultures had the following number of living cells:

C6+C11: (208.3±33.19)×10³, cell growth inhibition was 45.3% (p<0.01).

C7+C11: (215.0±13.39)×10³, cell growth inhibition was 43.5% (p<0.001).

C8+C11: (238.3±25.36)×10³, cell growth inhibition was 37.4% (p<0.01).

C9+C11: (244.2±21.63)×10³, cell growth inhibition was 35.8% (p<0.01).

C10+C11: (254.6±19.40)×10³, cell growth inhibition was 33.1% (p<0.01).

Thus, the preparations of C6+C11, C7+C11, C8+C11, C9+C11 and C10+C11 that were added to cultures in small concentrations, exert a pronounced cytotoxic action against human tumour cells since the number of cells in treated cultures was significantly decreased as compared to controls.

Example 15

The Cytotoxicity of Preparations of C6+C12, C7+C12, C8+C12, C9+C12 and C10+C12 in Cultures of HeLa Cell Line of Human Cervical Carcinoma After cultivation of HeLa cells for 24 h, the assayed cultures were treated with solutions of the preparations C6+C12, C7+C12, C8+C12, C9+C12 and C10+C12 in NBS The initial solutions of the preparations had a concentration of C6, C7, C8, C9, C10 and C12 equal to 0.5 mg/ml. From those solutions a working solution of each preparation in NBS was prepared for adding to cultures:

C6+C12: $6.12 \times 10^{-8}$ mol/l of C6 and $5.00 \times 10^{-8}$ mol/l of C12;

C7+C12: $6.47 \times 10^{-8}$ mol/l of C7 and $5.00 \times 10^{-8}$ mol/l of C12;

C8+C12: $6.44 \times 10^{-8}$ mol/l of C8 and $5.00 \times 10^{-8}$ mol/l of C12;

C9+C12: $6.83 \times 10^{-8}$ mol/l of C9 and $5.00 \times 10^{-8}$ mol/l of C12;

C10+C12: $6.83 \times 10^{-8}$ mol/l of C10 and $5.00 \times 10^{-8}$ mol/l of C12.

20 μl aliquots of these working solutions were added to 2 ml cultures of HeLa cells to a final concentration in the cultures:

C6+C12: $6.12 \times 10^{-10}$ mol/l of C6 and $5.00 \times 10^{-10}$ mol/l of C12;

C7+C12: $6.47 \times 10^{-10}$ mol/l of C7 and $5.00 \times 10^{-10}$ mol/l of C12;

C8+C12: $6.44 \times 10^{-10}$ mol/l of C8 and $5.00 \times 10^{-10}$ mol/l of C12;

C9+C12: $6.83 \times 10^{-10}$ mol/l of C9 and $5.00 \times 10^{-10}$ mol/l of C12;

C10+C12: $6.83 \times 10^{-10}$ mol/l of C10 and $5.00 \times 10^{-10}$ mol/l of C12.

In the control cultures, 20 μl of NBS was added as a solvent-control. After two days of following cultivation, the number of living cells in cultures was counted and the extent of growth inhibition of HeLa cells was calculated for evaluating the cytotoxicity of the assayed preparations.

After tree days of cultivation, the control cultures contained (399.4±31.01)×10³ cells.

The treated cultures had the following number of living cells:

C6+C12: (228.8±24.65)×10³, cell growth inhibition was 42.7% (p<0.01).

C7+C12: (239.4±29.12)×10³, cell growth inhibition was 40.1% (p<0.01).

C8+C12: (256.9±31.74)×10³, cell growth inhibition was 35.7% (p<0.02).

C9+C12: (278.7±24.40)×10³, cell growth inhibition was 30.2% (p<0.02).

C10+C12: (273.6±23.72)×10³, cell growth inhibition was 31.5% (p<0.02).

Thus, the preparations of C6+C12, C7+C12, C8+C12, C9+C12, C10+C12 , that were added to cultures in small concentrations, exert a pronounced cytotoxic action against human tumor cells since a number of cells in treated cultures was significantly decreased as compared to control.

C: In Vivo Studies

Materials and Methods

The antitumour effects of the compositions C1+C11, C2+C11, C3+C11, C4+C11, C5+C11, C6+C11, C7+C11, C8+C11, C9+C11, C10+C11, C1+C12, C2+C12, C3+C12, C4+C12, C5+C12, C6+C12, C7+C12, C8+C12, C9+C12 and C10+C12 in IRC mice with Ehrlich ascites carcinoma (EAC) were studied during the priority year.

Randombred albino mice of the ICR line, female, from own rearing were used in the study. The room for animal housing is provided with filtered air at 15 changes per hour, temperature of 19–21° C., relative humidity of 50–60% and regulated light day of 12 hours with change of light and darkness at 6 h a.m. and 6 h p.m. The mice were kept in transparent polycarbonate cages with floor area of 600 $cm^2$ containing softwood sawdust bedding. The animals had free access to bottles with domestic quality drinking tap water and to standard feeding for growing animals ad libidum. The mice age 2–2.5 months, weighing 20–23 g were randomly distributed to the control and test groups, standardised by mean weights. The control and test groups included 15 and 12 animals respectively. Specific earmarks identified the mice from each group. The cages with animals of each group were identified by cage cards marked with the study date, group number, number and sex of the animals.

The strain of EAC, that is hyperdiploid variant, was propagated in ICR mice by intraperitoneal inoculation of 0.2 ml native ascites fluid or diluted by saline to 1:1 from one animal with intraperitoneally growing EAC on day 7. Ascites fluids contained more 98% of viable tumour cells according to trypan blue exclusion test. For each assay the suspension of EAC cells in sterile saline in concentration of $10^7$ viable tumour cells/ml was prepared in aseptic conditions from ascites fluid of mouse bearing EAC on day 7.

The mice both control and experimental groups were inoculated by intraperitoneal injection of $2 \times 10^6$ EAC cells in volume of 0.2 ml at day 0. Intravenous injections were carried out in the lateral tail vein of mice once every other day, four times (day 1, 3, 5 and 7) following inoculation of EAC cells.

The mice from the control group were injected by vehicle (normal mice serum, NMS) in volume of 5 ml/kg of body weight (100 μl to mouse of 20 g body weight) intravenously (negative control).

The mice from the test groups received the compositions of C1+C11, C2+C11, C3+C11, C4+C11, C5+C11, C6+C11, C7+C11, C8+C11, C9+C11, C10+C11, C1+C12, C2+C12, C3+C12, C4+C12, C5+C12, C6+C12, C7+C12, C8+C12, C9+C12 and C10+C12 intravenously in the volume of 5 ml/kg of body weight (100 μl to mouse of 20 g body weight) on day 1, 3, 5 and 7. Each composition contained compound C11 or C12 in concentration 0,8 mg/ml and one compound of row C1–C10 in concentration 0,4 mg/ml in NMS.

The effect of pretreatment with the compositions C6+C11, C7+C11, C8+C11, C9+C11, C10+C11, C6+C12, C7+C12, C8+C12, C9+C12 and C10+C12 on the antitumour action of DXR in IRC mice with EAC have been studied.

The mice from the control group were injected by vehicle in volume of 5 ml/kg of body weight (100 μl to mouse of 20 g body weight) intravenously (negative control).

Other group of animals (positive control) received water solution of DXR (concentration of 0.7 mg/ml) in the dose of 3.5 mg/kg of body weight and in volume of 5 ml/kg of body weight intravenously on day 1, 3, 5 and 7.

The mice from the test groups received DXR alone in the same dose on day 1 and 5. The compositions C6+C11, C7+C11, C8+C11, C9+C11, C10+C11, C6+C12, C7+C12, C8+C12, C9+C12 and C10+C12 were injected intravenously in the volume of 5 ml/kg of body weight (100 μl to mouse of 20 g body weight) on day 3, and 7. Each composition contained compound C11 or C12 in concentration 1,5 mg/ml and one compound of row C6–C10 in concentration 0,7 mg/ml. At first, the composition was injected (pretreatment) and within 15 minutes after that mice were injected by water solution of DXR (concentration of 0.7 mg/ml) in the dose of 3.5 mg/kg and in volume of 5 ml/kg of body weight on day 3 and 7.

The mice were killed by cervical dislocation one day later after the final treatment with the test substances on day 8. Ascites fluids were removed, collected, their volumes were recorded, and abdominal cavities were washed by saline 6–7 times and both fluids were pooled. Volumes of tumour cell pellet after centrifugation at 1000 r.p.m. for 10 min were also recorded. Number of viable tumour cells was counted by haemocytometer. Means and standard errors for each of animal groups were calculated. Comparison of the tumour cell number in control and test groups was carried out using Student's t-test. Influence of the composition on EAC growth inhibition was evaluated by:

$$\text{Inhibition, \%} = \frac{\text{Control} - \text{Test}}{\text{Control}} \times 100$$

The extent of inhibition of EAC growth in mice was used for evaluation of antitumour activity of tested composition.

Example 16

Antitumour Effect of Compositions C1+C11, C2+C11 and C3+C11

Mice IRC of 20–22 g were inoculated intraperitoneally with $2 \times 10^6$ viable EAC cells. Starting on day 1, the mice were injected intravenously (in the volume of 5 ml/kg of body weight) once every other day, four times (day 1, 3, 5 and 7). Mice in the control group received vehicle (NMS). Mice in the test groups received one of the compositions C1+C11, C2+C11, C3+C11 in NMS (C1, C2 and C3—2 mg/kg; C11—4 mg/kg). On the day following final treatment with the compositions, the mice were killed by cervical dislocation (day 8). Tumour cell number was counted and the extent of inhibition of EAC growth in mice evaluated.

Mice in the control group had $(1061.7 \pm 82.4) \times 10^6$ EAC cells in the abdominal cavity. In mice in the C1+C11 test group the number of tumour cells was $(728.8 \pm 93.6) \times 10^6$ and EAC growth inhibition of 31.4%, $p < 0.02$. In mice in the C2+C11 test group the number of tumour cells was $(736.2 \pm 125.3) \times 10^6$ and EAC growth inhibition of 30.7%, $p < 0.05$. In mice in the C3+C11 test group the number of tumour cells was $(766.4 \pm 103.9) \times 10^6$ and EAC growth inhibition of 27.8%, $p < 0.05$.

Thus, the compositions C1+C11, C2+C11 and C3+C11 display marked antitumour action against EAC. The extent of tumour inhibition is about 30%.

Example 17

Antitumour Effect of Compositions C1+C12, C2+C12 and C3+C12

Mice IRC of 20–23 g were inoculated intraperitoneally with $2 \times 10^6$ viable EAC cells. Starting on day 1, the mice were injected intravenously (in the volume of 5 ml/kg of body weight) once every other day, four times (day 1, 3, 5 and 7). Mice from the control group received vehicle (NMS). Mice in the test groups received one of the compositions C1+C12, C2+C12, C3+C12 in NMS (C1, C2 and C3—2 mg/kg; C12—4 mg/kg). On the day following final treatment with the compositions, the mice were killed by cervical dislocation (day 8). Tumour cell number was counted and the extent of inhibition of EAC growth in mice was evaluated.

Mice in the control group had $(893.4\pm75.5)\times10^6$ EAC cells in the abdominal cavity. In mice in the C1+C12 test group the number of tumour cells was $(630.7\pm84.1)\times10^6$ and EAC growth inhibition of 29.4%, $p<0.05$. In mice in the C2+C12 test group the number of tumour cells was $(633.4\pm98.0)\times10^6$ and EAC growth inhibition of 29.1%, $p<0.05$. In mice in the C3+C12 test group the number of tumour cells was $(654.8\pm86.3)\times10^6$ and EAC growth inhibition of 26.7%, $p<0.05$.

Thus, the compositions C1+C12, C2+C12 and C3+C12 are shown to display marked antitumour action against EAC. The extent of tumour inhibition is close to 30%.

Example 18
Antitumour Effect of Compositions C4+C11 and C5+C11

Mice IRC of 20–22 g were inoculated intraperitoneally with $2\times10^6$ viable EAC cells. Starting on day 1, the mice were injected intravenously (in the volume of 5 ml/kg of body weight) once every other day, four times (day 1, 3, 5 and 7). Mice in the control group received vehicle (NMS). Mice in the test groups received one of the compositions C4+C11, C5+C11 in NMS (C4 and C5–2 mg/kg; C11–4 mg/kg). On next day following final treatment with the compositions, the mice were killed by cervical dislocation (day 8). Tumour cell number was counted and the extent of inhibition of EAC growth in mice was evaluated.

Mice in the control group had $(965.1\pm69.8)\times10^6$ EAC cells in abdominal cavity. In mice in the C4+C11 test group the number of tumour cells was $(700.6\pm77.8)\times10^6$ and EAC growth inhibition of 27.4%, $p<0.02$. In mice in the C5+C11 test group the number of tumour cells was $(694.8\pm96.5)\times10^6$ and EAC growth inhibition of 28.0%, $p<0.05$.

Thus, the compositions C4+C11 and C5+C11 were shown to display marked antitumour action against EAC. The extent of tumour inhibition is about 28%.

Example 19
Antitumour Effect of Compositions C4+C12 and C5+C12

Mice IRC of 20–22 g were inoculated intraperitoneally with $2\times10^6$ viable EAC cells. Starting on day 1, the mice were injected intravenously (in the volume of 5 ml/kg of body weight) once every other day, four times (day 1, 3, 5 and 7). Mice in the control group received vehicle (NMS). Mice in the test groups received one of the compositions C4+C12, C5+C12 in NMS (C4 and C5—2 mg/kg; C12—4 mg/kg). On the day following final treatment with the compositions mice were killed by cervical dislocation (day 8). Tumour cell number was counted and the extent of inhibition of EAC growth in mice was evaluated.

Mice in the control group had $(811.6\pm68.2)\times10^6$ EAC cells in abdominal cavity. In mice in the C4+C12 test group the number of tumour cells was $(603.0\pm73.4)\times10^6$ and EAC growth inhibition of 25.7%, $p<0.05$. In mice in the C5+C12 test group the number of tumour cells was $(597.1\mp70.7)\times10^6$ and EAC growth inhibition of 26.4%, $p<0.05$.

Thus, the compositions C4+C12 and C5+C12 were shown to display pronounced antitumour action against EAC. The extent of tumour inhibition is about 26%.

Example 20
Antitumour Effect of Compositions C6+C11, C7+C11 and C8+C11

Mice IRC of 20–22 g were inoculated intraperitoneally with $2\times10^6$ viable EAC cells. Starting on day 1, the mice were injected intravenously (in the volume of 5 ml/kg of body weight) once every other day, four times (day 1, 3, 5 and 7). Mice in the control group received vehicle (NMS). Mice in the test groups received one of the compositions C6+C11, C7+C11, C8+C11 in NMS (C6, C7 and C8—2 mg/kg; C11—4 mg/kg). On the next day after final treatment with the compositions, the mice were killed by cervical dislocation (day 8). Tumour cell number was counted and the extent of inhibition of EAC growth in mice was evaluated.

Mice in the control group had $(1124.8\pm92.7)\times10^6$ EAC cells in abdominal cavity. In mice in the C6+C11 test group the number of tumour cells was $(806.3\pm109.6)\times10^6$ and EAC growth inhibition of 28.3%, $p<0.05$. In mice in the C7+C11 test group the number of tumour cells was $(833.5\pm103.2)\times10^6$ and EAC growth inhibition of 25.9%, $p<0.05$. In mice in the C8+C11 test group the number of tumour cells was $(826.9\pm94.8)\times10^6$ and EAC growth inhibition of 26.5%, $p<0.05$.

Thus, the compositions C6+C11, C7+C11 and C8+C11 were shown to display pronounced antitumour action against EAC. The extent of tumour inhibition is close to 28%.

Example 21
Antitumour Effect of Compositions C6+C12, C7+C12 and C8+C12

Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle (NMS). Mice from the test groups received one of the compositions C6+C12, C7+C12, C8+C12 in NMS (C6, C7 and C8—2 mg/kg; C12—4 mg/kg). On the next day after final treatment with the compositions, the mice were killed by cervical dislocation (day 8). The tumour cell number was counted and the extent of inhibition of EAC growth in mice was evaluated.

Mice from the control group had $(1028.5\pm87.6)\times10^6$ EAC cells in abdominal cavity. In mice from the C6+C12 test group the number of tumour cells was $(745.4\pm81.3)\times10^6$ and EAC growth inhibition of 27.5%, $p<0.05$. In mice from the C7+C12 test group the number of tumour cells was $(741.2\pm106.6)\times10^6$ and EAC growth inhibition of 27.9%, $p<0.05$. In mice from the C8+C12 test group the number of tumour cells was $(769.1\pm85.4)\times10^6$ and EAC growth inhibition of 25.2%, $p<0.05$.

Thus, the compositions C6+C12, C7+C12 and C8+C12 display pronounced antitumour action against EAC. The extent of tumour inhibition is close to 27%.

Example 22
Antitumour Effects of Compositions C9+C11 and C10+C11

Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle (NMS). Mice from the test groups received one of the compositions C9+C11, C10+C11 in NMS (C9 and C10—2 mg/kg; C11—4 mg/kg). On next day after final treatment with the compositions mice were killed by cervical dislocation on day 8. Tumour cell number was counted and the extent of inhibition of EAC growth in mice was evaluated.

Mice from the control group had $(973.0\pm62.3)\times10^6$ EAC cells in abdominal cavity. In mice from the C9+C11 test group the number of tumour cells was $(776.9\pm58.5)\times10^6$ and EAC growth inhibition of 20.2%, p<0.05. In mice from the C10+C11 test group the number of tumour cells was $(789.7\pm60.4)\times10^6$ and EAC growth inhibition of 18.8%, p<0.05. Thus, the compositions C9+C11 and C10+C11 display significant antitumour action against EAC. The extent of tumour inhibition is close to 20%.

Example 23
Antitumour Effect of Compositions C9+C12 and C10+C12

Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle (NMS). Mice from the test groups received one of the copmositions C9+C12, C10+C12 in NMS (C9 and C10—2 mg/kg; C12—4 mg/kg). On next day after final treatment with the compostions mice were killed by cervical dislocation on day 8. Tumour cell number was counted and the extent of inhibition of EAC growth in mice was evaluated.

Mice from the control group had $1007.3\pm65.1)\times10^6$ EAC cells in abdominal cavity. In mice from the C9+C12 test group the number of tumour cells was $(775.6\pm73.0)\times10^6$ and EAC growth inhibition of 23.0%, p<0.05. In mice from the C10+C12 test group the number of tumour cells was $(831.2\pm53.9)\times10$ and EAC growth inhibition of 17.5%, p<0.05.

Thus, the compositions C9+C12 and C10+C12 display significant antitumour action against EAC. The extent of tumour inhibition is close to 23%.

Example 24
The Influence of Pretreatment with the Compositions C6+C11 and C7+C11 on Antitumour Effect of Doxorubicin (DXR)

Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle. Other group of animals (positive control) received DXR in the dose of 3.5 mg/kg of body weight (70 $\mu$g of DXR to mouse of 20 g body weight) intravenously. Mice from the test groups received one of the compositions C6+C11, C7+C11 (C6 and C7—3.5 mg/kg; C11—7.5 mg/kg) at first (pretreatment) and within 15 minutes after that mice were injected by DXR in the dose of 3.5 mg/kg of body weight (70 $\mu$g of DXR in 100 $\mu$l to mouse of 20 g body weight). On next day after final treatment mice were killed by cervical dislocation on day 8. Tumour cell number was counted and the extent of inhibition of EAC growth in mice was evaluated.

Mice from the control group had $(918.1\pm93.7)\times10^6$ EAC cells in abdominal cavity. In other group of mice with DXR alone (positive control) the number of tumour cells was $(525.2\pm74.5)\times10^6$ and EAC growth inhibition of 42.8%, p<0.01. In mice from the C6+C11 test group the number of tumour cells was $(318.3\pm61.5)\times10^6$ and EAC growth inhibition of 65.3%, p<0.001. The extent of tumour inhibition compared to that of DXR was increased 39.4%, p<0.05. In mice from the C7+C11 test group the number of tumour cells was $(342.9\pm46.1)\times10^6$ and EAC growth inhibition of 62.7%, p<0.001. The extent of tumour inhibition compared to that of DXR was increased 34.7%, p<0.05.

Thus, the pretreatment with the compositions C6+C11 and C7+C11 display marked increase of antitumour action of DXR against EAC close to 40%.

Example 25
The Influence of Pretreatment with the Compositions C6+C12 and C7+C12 on Antitumour Effect of DXR Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle. Other group of animals (positive control) received DXR in the dose of 3.5 mg/kg of body weight (70 $\mu$g of DXR to mouse of 20 g body weight) intravenously. Mice from the test groups received one of the compositions C6+C12, C7+C12 (C6 and C7—3.5 mg/kg; C12—7.5 mg/kg) at first (pretreatment) and within 15 minutes after that mice were injected by DXR in the dose of 3.5 mg/kg of body weight (70 $\mu$g of DXR in 100 $\mu$l to mouse of 20 g body weight). On next day after final treatment mice were killed by cervical dislocation on day 8. Tumour cell number was counted and the extent of inhibition of EAC growth in mice was evaluated.

Mice from the control group had $(794.7\pm118.3)\times10^6$ EAC cells in abdominal cavity. In other group of mice with DXR alone (positive control) the number of tumour cells was $(436.3\pm51.8)\times10^6$ and EAC growth inhibition of 45.1%, p<0.02. In mice from the C6+C12 test group the number of tumour cells was $(275.4\pm49.7)\times10^6$ and EAC growth inhibition of 65.3%, p<0.001. The extent of tumour inhibition compared to that of DXR was increased 36.9%, p<0.05. In mice from the C7+C12 test group the number of tumour cells was $(295.8\pm43.3)\times10^6$ and EAC growth inhibition of 62.8%, p<0.001, The extent of tumour inhibition compared to that of DXR was increased 32.2% p<0.05.

Thus, the pretreatment with the compositions C6+C12 and C7+C12 display marked increase of antitumour action of DXR against EAC close to 37%.

Example 26
The Influence of Pretreatment with the Compositions C8+C11 and C9+C11 on Antitumour Effect of DXR Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle. Other group of animals (positive control) received DXR in the dose of 3.5 mg/kg of body weight (70 $\mu$g of DXR to mouse of 20 g body weight) intravenously. Mice from the test groups received one of the compositions C8+C11, C9+C11 (C8 and C9—3.5 mg/kg; C11—7.5 mg/kg) at first (pretreatment) and within 15 minutes after that mice were injected by DXR in the dose of 3.5 mg/kg of body weight (70 $\mu$g of DXR in 100 $\mu$l to mouse of 20 g body weight). On next day after final treatment mice were killed by cervical dislocation on day 8. Tumour cell number was counted and the extent of inhibition of EAC growth in mice was evaluated.

Mice from the control group had $(1165.8\pm139.4)\times10^6$ EAC cells in abdominal cavity. In other group of mice with DXR alone (positive control) the number of tumour cells was $(614.4\pm60.2)\times10^6$ and EAC growth inhibition of 47.3%, p<0.002. In mice from the C8+C11 test group the number of tumour cells was $(408.5\pm58.7)\times10^6$ and EAC growth inhibition of 65.0%, p<0.001, The extent of tumour inhibition compared to that of DXR was increased 33.5%, p<0.05. In mice from the C9+C11 test group the number of tumour cells was $(443.6\pm52.6)\times10^6$ and EAC growth inhibition of 61.9%, p<0.001, The extent of tumour inhibition compared to that of DXR was increased 27.8%, p<0.05.

Thus, the pretreatment with the compositions C8+C11 and C9+C11 display marked increase of antitumour action of DXR against EAC close to 33%.

Example 27
The Influence of Pretreatment with the Compositions C8+C12 and C9+C12 on Antitumour Effect of DXR Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle. Other group of animals (positive control) received DXR in the dose of 3.5 mg/kg of body weight (70 μg of DXR to mouse of 20 g body weight) intravenously. Mice from the test groups received one of the compositions C8+C12, C9+C12 (C8 and C9—3.5 mg/kg; C12—7.5 mg/kg) at first (pretreatment) and within 15 minutes after that mice were injected by DXR in the dose of 3.5 mg/kg of body weight (70 μg of DXR in 100 μl to mouse of 20 g body weight). On next day after final treatment mice were killed by cervical dislocation on day 8. Tumour cell number was counted and the extent of inhibition of EAC growth in mice was evaluated.

Mice from the control group had $(895.4\pm126.1)\times10^6$ EAC cells in abdominal cavity. In other group of mice with DXR alone (positive control) the number of tumour cells was $(542.6\pm50.1)\times10^6$ and EAC growth inhibition of 39.4%, $p<0.02$. In mice from the C8+C12 test group the number of tumour cells was $(384.7\pm47.5)\times10^6$ and EAC growth inhibition of 57.0%, $p<0.002$. The extent of tumour inhibition compared to that of DXR was increased 29.1%, $p<0.05$. In mice from the C9+C12 test group the number of tumour cells was $(399.8\pm45.9)\times10^6$ and EAC growth inhibition of 55.3%, $p<0.002$. The extent of tumour inhibition compared to that of DXR was increased 26.3%, $p<0.05$.

Thus, the pretreatment with the compositions C8+C12 and C9+C12 display marked increase of antitumour action of DXR against EAC close to 29%.

Example 28
The Influence of Pretreatment with the Compositions C10+C11 and C10+C12 on Antitumour Effect of DXR Mice IRC of 20–22 g were inoculated intraperitoneally with $2\times10^6$ viable EAC cells. Starting day 1 mice were injected intravenously (in the volume of 5 ml/kg of body weight) once every other day, four times (day 1, 3, 5 and 7). Mice from the control group received vehicle. Other group of animals (positive control) received DXR in the dose of 3.5 mg/kg of body weight (70 μg of DXR to mouse of 20 g body weight) intravenously. Mice from the test groups received one of the compositions C10+C11, C10+C12 (C10—3.5 mg/kg; C11 and C12—7.5 mg/kg) at first (pretreatment) and within 15 minutes after that mice were injected by DXR in the dose of 3.5 mg/kg of body weight (70 μg of DXR in 100 μl to mouse of 20 g body weight). On next day after final treatment mice were killed by cervical dislocation on day 8. Tumour cell number was counted and the extent of inhibition of EAC growth in mice was evaluated.

Mice from the control group had $(963.6\pm129.6)\times10^6$ EAC cells in abdominal cavity. In other group of mice with DXR alone (positive control) the number of tumour cells was $(534.8\pm39.3)\times10^6$ and EAC growth inhibition of 44.5%, $p<0.01$. In mice from the C10+C11 test group the number of tumour cells was $(400.1\pm50.2)\times10^6$ and EAC growth inhibition of 58.5%, $p<0.001$. The extent of tumour inhibition compared to that of DXR was increased 25.2%, $p<0.05$. In mice from the C10+C12 test group the number of tumour cells was $(401.6\pm50.0)\times10^6$ and EAC growth inhibition of 58.3%, $p<0.001$. The extent of tumour inhibition compared to that of DXR was increased of 24.9%, $p<0.05$.

Thus, the pretreatment by compositions C10+C11 and C10+C12 display marked increase of antitumour action of DXR against EAC about 25%.

Although the invention has been described with regard to its preferred embodiments, which constitute the best mode presently known to the inventor, it should be understood that various changes and modifications as would be obvious to one having the ordinary skill in this art may be made without departing from the scope of the invention as set forth in the claims appended hereto.

REFERENCES

Chattopadhyay A. and London E. Anal.Biochem., 1984, 139, p.408–412

Das U. N., et al., *Prostaglandins Leukot. Essent. Fatty Acids*, 58, 39–54, 1998

Germain E., et al., *Int. J. Cancer*, 75, 578–583, 1998

Gore J., et al., *Amer. J. Physiol.*, 266, C110–C120, 1994

Nietgen G. W., Durieux M. E., *Cell Adhesion and Communication*, 5,221–235, 1998

Petersen E. S., et al., *Cancer Res.*, 42, 6263–6269, 1992

Shao Y., et al., *Lipids*, 30, 1035–1045, 1995

What is claimed is:

1. A method for treating a patient suffering from cancer, said method comprising the step of administering to the patient an effective amount of a compound selected from the group consisting of N-docosahexaenoyl-cysteamine-S-phosphate, N-eicosapentaenoyl-cysteamine-S-phosphate, N-arachidonoyl-cysteamine-S-phosphate, N-α-linolenoyl-cysteamine-S-phosphate, and N-γ-linolenoyl-cysteamine-S-phosphate.

2. A method for treating a patient suffering from cancer, said method comprising the step of administering to the patient an effective amount of a compound selected from the group consisting of N-docosahexaenoyl-cysteamine-S-phosphate, N-eicosapentaenoyl-cysteamine-S-phosphate, N-arachidonoyl-cysteamine-S-phosphate, N-α-linolenoyl-cysteamine-S-phosphate, and N-γ-linolenoyl-cysteamine-S-phosphate in admixture or simultaneously with N-(all-trans-retinoyl)-O-phospho-L-tyrosine.

3. A method for treating a patient suffering from cancer, said method comprising the step of administering to the patient an effective amount of a compound selected from the group consisting of N-docosahexaenoyl-cysteamine-S-phosphate, N-eicosapentaenoyl-cysteamine-S-phosphate, N-arachidonoyl-cysteamine-S-phosphate, N-α-linolenoyl-cysteamine-S-phosphate, and N-γ-linolenoyl-cysteamine-S-phosphate in admixture or simultaneously with N-(13-cis-retinoyl)-O-phospho-L-tyrosine.

4. A substantially pure compound selected from the group consisting of N-docosahexaenoyl-cysteamine-S-phosphate, N-eicosapentaenoyl-cysteamine-S-phosphate, N-arachidonoyl-cysteamine-S-phosphate, N-α-linolenoyl-cysteamine-S-phosphate, and N-γ-linolenoyl-cysteamine-S-phosphate.

5. A pharmaceutical preparation, characterized in that it comprises a therapeutically effective amount of a compound according to claim 1.

6. A pharmaceutical preparation, characterized in that it comprises a therapeutically effective amount of a compound according to claim 1 in micellar form.

7. A pharmaceutical preparation, characterized in that it comprises a therapeutically effective amount of a compound selected from the group consisting of N-docosahexaenoyl-O-phospho-2-aminoethanol, N— eicosapentaenoyl O-phospho-2-aminoethanol, N-arachidonoyl O-phospho-2-aminoethanol, N-α-linolenoyl O-phospho-2-aminoethanol, and N-γ-linolenoyl O-phospho-2-aminoethanol.

8. A pharmaceutical preparation according to claim 4, characterized in that it comprises the therapeutically effective amount of the selected compound in micellar form.

9. A pharmaceutical preparation, characterized in that it comprises a therapeutically effective amount of a compound according to claim 1 in combination with a therapeutically effective amount of N-(all-trans-retinoyl)-O-phospho-L-tyrosine.

10. A pharmaceutical preparation, characterized in that it comprises a therapeutically effective amount of a compound according to claim 1 in combination with a therapeutically effective amount of N-(13-cis-retinoyl)-O-phospho-L-tyrosine.

11. A pharmaceutical preparation, characterized in that it comprises a therapeutically effective amount of a compound selected from the group consisting of N-docosahexaenoyl-O-phospho-2-aminoethanol, N-eicosapentaenoyl O-phospho-2-aminoethanol, N-arachidonoyl O-phospho-2-aminoethanol, N-α-linolenoyl O-phospho-2-aminoethanol, and N-γ-linolenoyl O-phospho-2-aminoethanol in combination with a therapeutically effective amount of N-(all-trans-retinoyl)-O-phospho-L-tyrosine.

12. A pharmaceutical preparation, characterized in that it comprises a therapeutically effective amount of a compound selected from the group consisting of N-docosahexaenoyl-O-phospho-2-aminoethanol, N-eicosapentaenoyl O-phospho-2-aminoethanol, N-arachidonoyl O-phospho-2-aminoethanol, N-α-linolenoyl O-phospho-2-aminoethanol, and N-γ-linolenoyl O-phospho-2-aminoethanol in combination with a therapeutically effective amount of N-(13-cis-retinoyl)-O-phospho-L-tyrosine.

13. A pharmaceutical preparation, characterized in that it comprises a therapeutically effective amount of N-docosahexaenoyl-cysteamine-S-phosphate and one of N-(all-trans-retinoyl)-O-phospho-L-tyrosine or N-(13-cis-retinoyl)-O-phospho-L-tyrosine.

14. A pharmaceutical preparation, characterized in that it comprises a therapeutically effective amount of N-eicosapentaenoyl-cysteamine-S-phosphate and one of N-(all-trans-retinoyl)-O-phospho-L-tyrosine or N-(13-cis-retinoyl)-O-phospho-L-tyrosine.

15. A pharmaceutical preparation, characterized in that it comprises a therapeutically effective amount of N-arachidonoyl-cysteamine-S-phosphate and one of N-(all-trans-retinoyl)-O-phospho-L-tyrosine or N-(13-cis-retinoyl)-O-phospho-L-tyrosine.

16. A pharmaceutical preparation, characterized in that it comprises a therapeutically effective amount of N-α-linolenoyl-cysteamine-S-phosphate and one of N-(all-trans-retinoyl)-O-phospho-L-tyrosine or N-(13-cis-retinoyl)-O-phospho-L-tyrosine.

17. A pharmaceutical preparation, characterized in that it comprises a therapeutically effective amount of N-γ-linolenoyl-cysteamine-S-phosphate and one of N-(all-trans-retinoyl)-O-phospho-L-tyrosine or N-(13-cis-retinoyl)-O-phospho-L-tyrosine.

18. Use of a compound according to claim 1 for the manufacture of a pharmaceutical preparation.

19. Use of a compound according to claim 1 for the manufacture of a pharmaceutical preparation for the treatment of cancer.

20. Use of a compound for the manufacture of a pharmaceutical preparation, said compound being selected from the group consisting of N-docosahexaenoyl-O-phospho-2-aminoethanol, N-eicosapentaenoyl O-phospho-2-aminoethanol, N-arachidonoyl O-phospho-2-aminoethanol, N-α-linolenoyl O-phospho-2-aminoethanol, and N-γ-linolenoyl O-phospho-2-aminoethanol.

21. Use of a compound for the manufacture of a pharmaceutical preparation for the treatment of cancer, said compound being selected from the group consisting of N-docosahexaenoyl-O-phospho-2-aminoethanol, N—eicosapentaenoyl O-phospho-2-aminoethanol, N-arachidonoyl O-phospho-2-aminoethanol, N-α-linolenoyl O-phospho-2-aminoethanol, and N-γ-linolenoyl O-phospho-2-aminoethanol.

22. A method for treating a patient suffering from cancer, said method comprising the step of administering to the patient an effective amount of a compound according to claim 7, in admixture with or substantially simultaneously with a cytotoxic agent.

23. A method for treating a patient suffering from cancer, said method comprising the step of administering to the patient an effective amount of a compound according to claim 11, in admixture with or substantially simultaneously with a cytotoxic agent.

24. A method for treating a patient suffering from cancer, said method comprising the step of administering to the patient an effective amount of a compound according to claim 8, in admixture with or substantially simultaneously with a cytotoxic agent.

25. A method for treating a patient suffering from cancer, said method comprising the step of administering to the patient an effective amount of a compound according to claim 12, in admixture with or substantially simultaneously with a cytotoxic agent.

26. The method of claim 22 wherein said cytotoxic agent is doxorubicin.

27. The method of claim 23 wherein said cytotoxic agent is doxorubicin.

28. The method of claim 24 wherein said cytotoxic agent is doxorubicin.

29. The method of claim 25 wherein said cytotoxic agent is doxorubicin.

* * * * *

UNITED STATES PATENT AND TRADEMARK OFFICE
CERTIFICATE OF CORRECTION

PATENT NO. : 6,699,851 B2
DATED : March 2, 2004
INVENTOR(S) : Oleg Strelchenok

It is certified that error appears in the above-identified patent and that said Letters Patent is hereby corrected as shown below:

Title page,
Item [56], References Cited, FOREIGN PATENT DOCUMENTS, please insert the following:
-- DE          DE 40 32 187 A1          4/1992 --.
OTHER PUBLICATIONS, please insert the following:
-- Arsenov et al. (2001) Pharm. Chem. J. (Engl. Transl.) 35(4):186-189 --.

Signed and Sealed this

Twenty-fifth Day of October, 2005

JON W. DUDAS
*Director of the United States Patent and Trademark Office*